United States Patent
Vahaviolos

[11] 3,965,726
[45] June 29, 1976

[54] METHOD AND APPARATUS FOR THE REAL-TIME EVALUATION OF WELDS BY EMITTED STRESS WAVES

[75] Inventor: Sotirios John Vahaviolos, East Windsor Township, Mercer County, N.J.

[73] Assignee: Western Electric Company, Inc., New York, N.Y.

[22] Filed: July 2, 1975

[21] Appl. No.: 592,437

[52] U.S. Cl. ................................................. 73/71.4
[51] Int. Cl.² .......................................... G01N 29/00
[58] Field of Search ............ 73/67, 67.2, 88.3, 71.4; 340/213 Q, 267 W

[56] References Cited
OTHER PUBLICATIONS

An Article "The Application of Acoustic Emission to In-Process Inspection of Welds" by W. Jolly, from Materials Evaluation, vol. 28, pp. 135–139, 144, June 1970.
"The Measurement of Energy in Acoustic Emission" by Beattie et al, from Review of Scientific Instruments, 3/74 pp. 352–357 (pp. 352–353).
"Acoustic Emission Tests Begin to be Heard" by Hartman from Iron Age, 9/74, pp. 43–45.
"Forecasting Failures with Acoustic Emission" by Herzog, from Machine Design, 6/73, pp. 132–137.

*Primary Examiner*—James J. Gill
*Attorney, Agent, or Firm*—E. W. Pfeifle; D. J. Kirk

[57] ABSTRACT

Spot welds are evaluated using stress-wave emission techniques by detecting and measuring the stress waves emitted from a weld area during a first solid-to-liquid phase transformation period and a second liquid-to-solid phase transformation period of the weld. The stress waves emitted during the first transformation period provide an indication of the weld nugget size, while the stress waves emitted during the second transformation period provides an indication of the amount of post-weld cracking in the weld area. By subtracting the stress-wave energy measured during the second transformation period from the stress-wave energy measured during the first transformation period, an indication of the strength of the weld is obtained.

10 Claims, 6 Drawing Figures

METHOD AND APPARATUS FOR THE REAL-TIME EVALUATION OF WELDS BY EMITTED STRESS WAVES

Background of the Invention

1. Field of the Invention

This invention relates to method and apparatus for the real-time, non-destructive evaluation of welds by stress-wave emission techniques, and more particularly, to method and apparatus which evaluates a weld by measuring stress waves emitted from the weld area during the solid-to-liquid phase transformation and the liquid-to-solid phase transformation of a weld.

2. Description of the Prior Art

The ability to evaluate a weld using real-time, non-destructive methods has always been of interest to industry. A method of monitoring a welding operation was disclosed in U.S. Pat. No. 3,726,130, issued to R. P. Hurlebaus on April 10, 1973. There, ultrasonic shear wave pulse signals are transmitted into the two pieces to be welded from a transducer positioned opposite the welding electrode while the welding operation is being performed. These signals are reflected from the area between the melting metal and the solid metal to provide real-time data for detecting the degree of penetration of a weld.

Another method for monitoring a welding operation was disclosed in an article entitled, "Forecasting Failures with Acoustic Emissions," by R. E. Herzog published in *machine design*, June 14, 1973, at pages 132–137. There it was stated that one of the more successful uses of acoustic emissions is in inspecting welds as they are being made by detecting and correlating signals emitted during the liquid-to-solid phase transformation of a weld area to indicate good or bad welds. The Herzog article further specifies that complex stress waves occur in both the weld cycle and post-weld cooling period, but only emissions during the post-weld cooling period are used for finding defects, such as cracks, as they occur in the weld area, and that emissions during the weld cycle are ignored.

The prior art method, using stress-wave emission techniques, therefore, only measures the amount of cracking which may occur in the weld area during the post-weld cooling period to determine if a weld is good or bad. The problem still remains of providing method and apparatus which will provide a more accurate real-time, non-destructive evaluation of both the strength and the quality of a weld.

Brief Summary of the Invention

The present invention relates to method and apparatus for the real-time, non-destructive evaluation of welds by stress-wave emission techniques, and more particularly, to method and apparatus which evaluates a weld by measuring stress waves emitted from the weld area during the solid-to-liquid phase transformation and the liquid-to-solid phase transformation of a weld.

The present invention further relates to method and apparatus for the real-time, non-destructive evaluation of a weld, wherein the stress waves emitted from the weld area during both a first solid-to-liquid phase transformation period and a subsequent second liquid-to-solid phase transformation period are measured, and the difference between the stress-wave energy measured during the first and the second transformation periods is compared with a predetermined reference value to determine the acceptability of a weld.

Other and further aspects of the present invention will become apparent during the course of the following description and by reference to the accompanying drawings and the appended claims.

Brief Description of the Drawings

Referring now to the drawings, in which like numerals represent like parts in the several views.

Description of the Preferred Embodiments

The welding process occurs by mechanically holding articles to be welded together, melting the parts at their common interface, causing molten material coflow, and resolidifying the molten volume. The volume where melting occurs is generally called the molten-resolidification zone or weld nugget, while the region where grain structure modification takes place is generally called the heat-affected zone. The required interfacial heat can be supplied in a number of different ways, one of which is by capacitor discharge welding where a pulse of high current is passed across the weld part interface. The present invention has been described primarily with relation to a capacitance discharge welding device. However, it will be understood that such description is exemplary only and is for the purposes of exposition and not for purposes of limitation. It will be readily appreciated that the inventive concept is equally applicable for use with any other welding apparatus, such as a laser.

Figure 1:
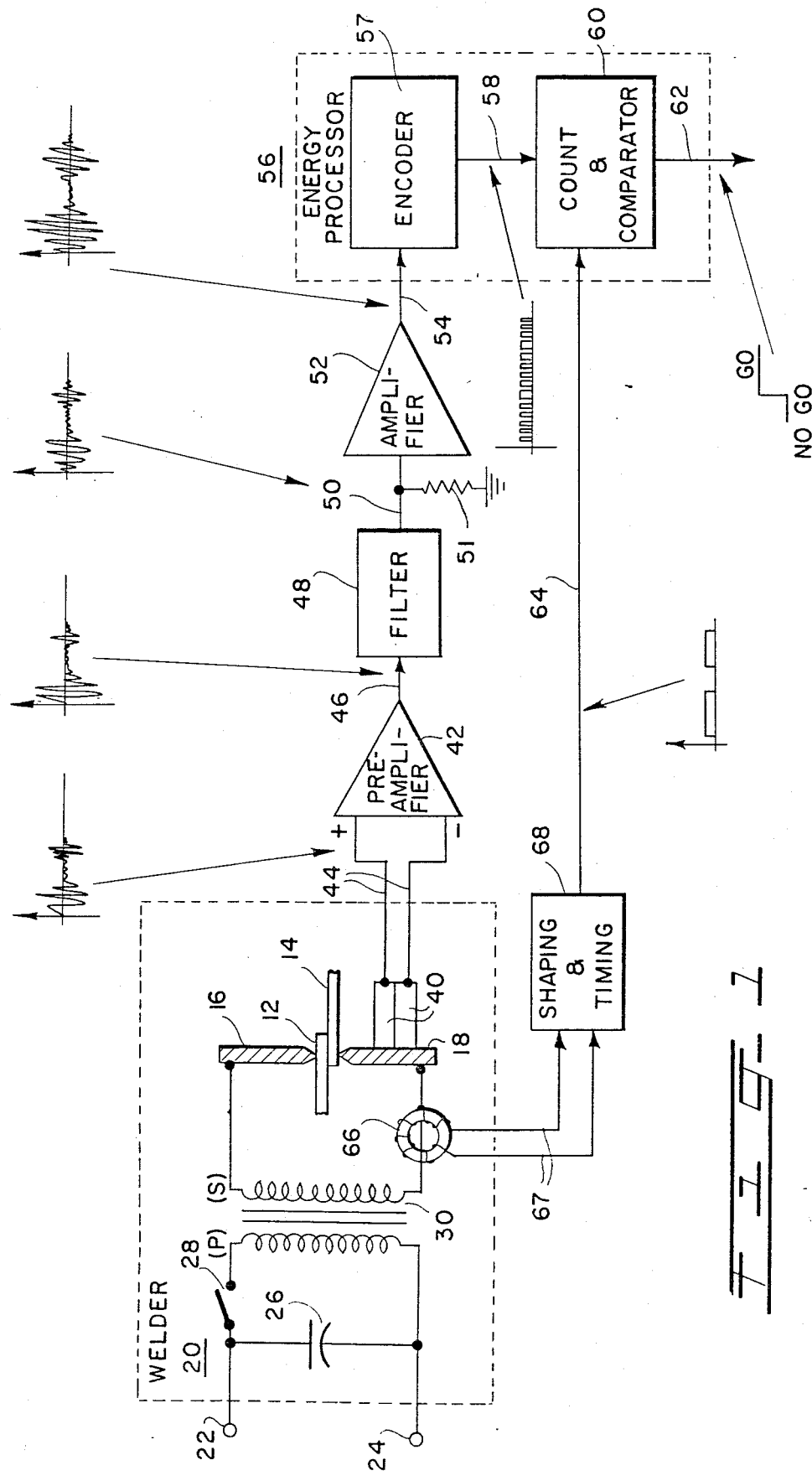
FIG. 1 is a simplified block diagram of a weld-evaluation system according to the present invention.

Referring now to FIG. 1, a pair of overlapping articles 12 and 14 comprising the same or different materials are positioned to be welded together between electrodes 16 and 18 of, for instance, a capacitance discharge welder 20. When a power source (not shown) is connected to terminals 22 and 24 of welder 20, capacitor 26 becomes charged. The closure of switch 28 discharges capacitor 26 through the primary winding (P) of transformer 30, causing a pulse of current to be delivered by the secondary winding (S) of transformer 30 to electrodes 16 and 18 and across the weld part interface. Capacitor 26 should be of sufficient size to deliver a pulse of current which will melt or plastically deform the weld area at the interface of articles 12 and 14.

Stress waves emitted from the weld area during both the weld pulse and post-weld intervals are detected by a piezoelectric differential transducer 40 (hereinafter referred to as sensor 40) of the present weld evaluation apparatus. Sensor 40 is shown as mechanically coupled to electrode 18 for non-contact detection purposes, but could also, for instance, be mechanically coupled to electrode 16 or either one of articles 12 and 14.

The signals which are detected by sensor 40 comprise waves which are: (a) generated by other electrical components in proximity to the system of FIG. 1, but not shown; (b) generated in articles 12 and 14, electrodes 16 and 18, or sensor 40 due to nontransient factors such as temperature and strain variations; and (c) stress waves, comprising bulk and surface waves, propagating from the weld nugget in articles 12 and 14, while the articles are being welded.

Whenever a phase transformation occurs in the weld nugget, energy is released in the form of stress waves, which waves, in turn, excite sensor 40. Depending on wave damping at the interfaces, the traveling mechanical stress impulses will cause sensor 40 to provide output voltage changes which are almost proportional to the amplitude of the impulses. Because of the low amplitude of the stress wave pulses, it is advantageous to provide for good transmission of the mechanical wave or amplification of the sensor's output voltage.

As shown in FIG. 1, sensor 40 is connected to a low-noise preamplifier 42 over leads 44. Preamplifier 42 should be of a design having a sensitivity which is preferably in the range of 1-4 $\mu$ V, but can include a sensitivity beyond this range, as for example, 6$\mu$V.

The output from preamplifier 42 is transmitted over lead 46 to a band-pass filter 48 which has a pass-band that falls at least partially within the natural frequency of sensor 40, but which falls without the range of noise frequencies generated by other components in proximity to the system. Filter 48 is preferably a fifth order, or higher, high-pass filter which is commercially available. A resistor 51 is preferably added to line 50 to match the input impedance of amplifier 52. The output of filter 48 on lead 50 is further amplified by amplifier 52. Amplifier 52 is of a design which advantageously has a fast slewing rate, such as, for example, a commercially available model 715 operational amplifier. The output of amplifier 52 is transmitted over lead 54 to an energy processor 56.

Energy processor 56 receives the amplified and filtered signal on lead 54 and measures the stress-wave energy released from the weld area during both the solid-to-liquid phase transformation and the post-weld liquid-to-solid phase transformation of the weld nugget.

Energy processor 56 can comprise circuitry which operates in accordance with a very fast analog-to-digital conversion scheme. Such circuitry, however, is very expensive.

Figure 3:
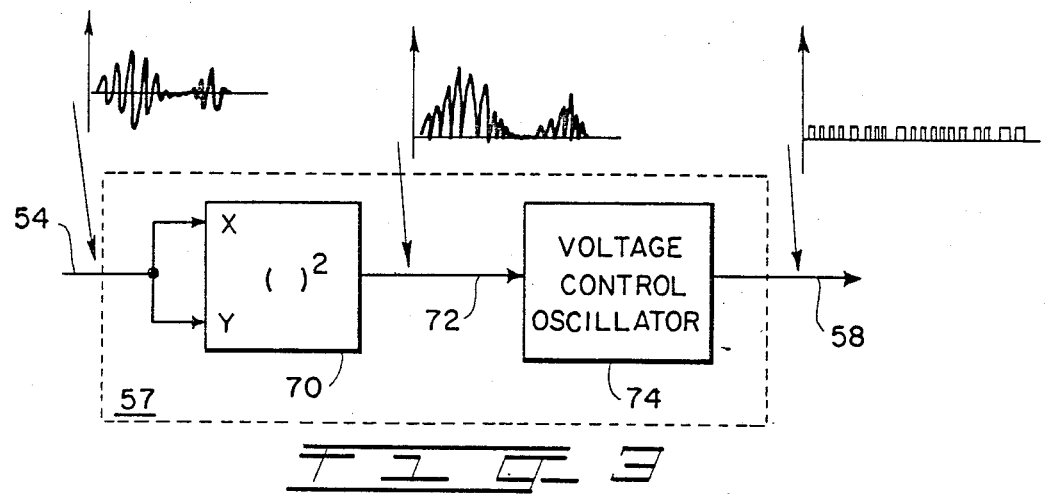
FIG. 3 is a simplified block diagram of an encoder for use with the energy processor of FIG. 1.
Figure 4:
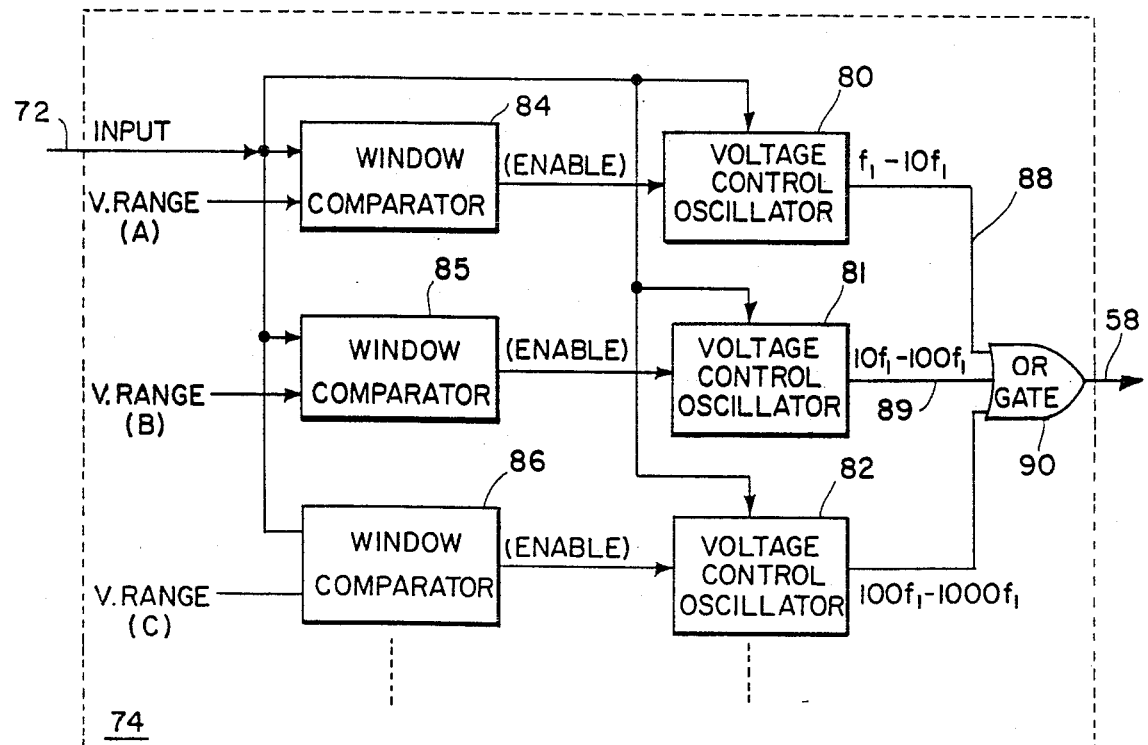
FIG. 4 is a simplified block diagram of a voltage control oscillator for use in the encoder of FIG. 3.

FIGS. 3 and 4 illustrate a novel energy processor 56 which provides very fast yet relatively inexpensive circuitry for use in the present weld evaluation system. Novel energy processor 56 includes an encoder 57 shown in FIG. 3 as comprising a multiplier circuit 70 which provides an output signal on lead 72 that is the square of the input signal on lead 54, and a voltage control oscillator 74. Multiplier 70 can comprise any known circuit such as, for example, a model 4456 multiplier from Teledyne-Philbric of Dedham, Mass. Voltage control oscillator 74 converts the squared amplitude modulated input signal on lead 72 into a digital frequency-modulated (FM) output signal, a change in the amplitude of the input signal causing a corresponding change in the rate, or frequency, of the digital pulses of the output signal.

Voltage control oscillator 74 should preferably comprise circuitry which provides a frequency range of approximately 1000:1. Since conventional voltage control oscillators generally provide a frequency range of up to 10:1, the novel voltage control oscillator circuitry 74 of FIG. 4 is preferably used in the present system. There, separate, commercially available voltage control oscillators (VCO) 80, 81, and 82 provide a digital FM output signal within the range of $f_1$ to $10f_1$, $10f_1$ to $100f_1$, and $100f_1$ to $1000f_1$, respectively. Each VCO 80, 81, and 82 has a separate respective window comparator 84, 85, and 86 associated therewith. Each window comparator 84, 85, and 86 compares the instantaneous voltage level of the input signal on lead 72 with a different portion of the overall input signal voltage range and provides an enable signal to the associated VCO 80–82 when the input voltage level falls within the associated voltage range under comparison. The input signal on lead 72 is also supplied to each of the VCOs 80–82.

In operation, if the input signal on lead 72 is assumed to include a voltage level which is rising through the entire ranges A and B, then window comparator 84 supplies an enable signal to VCO 80 for as long as the input voltage level is rising within range A. The enable signal from window comparator 84 causes VCO 80 to generate a digital FM output signal on lead 88 which increases from $f_1$ to $10f_1$ as the input voltage level correspondingly increases through range A. When the input voltage level reaches the lower edge of range B, window comparator 84 ceases to generate an enable signal to VCO 80 and window comparator 85 now supplies an enable signal to VCO 81. The enable signal from window comparator 85 causes VCO 81 to generate a digital FM output signal on lead 89 which increases from $10f_1$ to $100f_1$ as the input voltage level correspondingly increases through range B. The output from each of VCOs 80–82 is coupled to a common OR-gate 90 and onto lead 58 for transmission to a count and comparator circuit 60 of energy processor 56 (FIG. 1). It is, of course, possible to add further window comparators and VCOs in a manner shown in FIG. 4 to extend the range of operation. The voltage control oscillator circuitry 74 avoids the use of integrators which are generally limited in bandwidth and accuracy.

Figure 5:
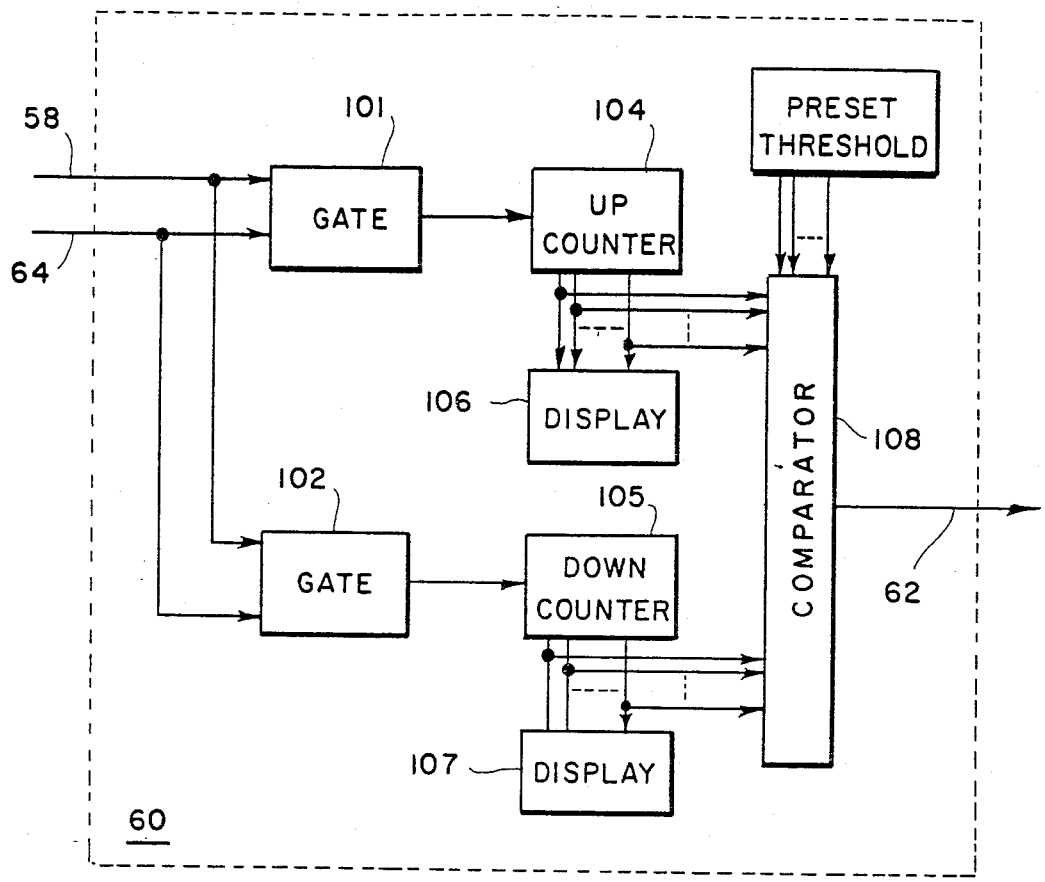
FIG. 5 is a simplified block diagram of a count and comparator circuit for use in the energy processor of FIG. 1.
Figure 6:
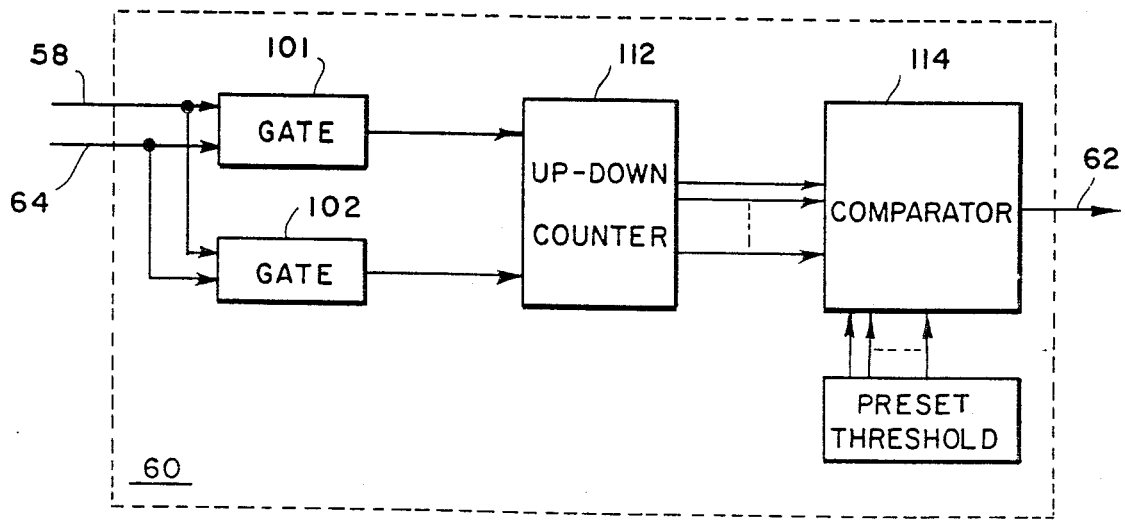
FIG. 6 is a simplified block diagram of another count and comparator circuit for use in the energy processor of FIG. 1.

The digital FM output signal from encoder 57 is transmitted over lead 58 to a count and comparator circuit 60 which forms another portion of energy processor 56. Count and comparator circuit 60 functions to separately count the input digital pulses relating to the solid-to-liquid phase transformation and the liquid-to-solid phase transformation of the weld, subtract the latter count from the former count, compare the net count value with a predetermined threshold value, and generate a go or no-go signal on lead 62 as a result of said comparison. FIGS. 5 and 6 illustrate two typical configurations which can be used in count and comparator circuit 60.

In FIGS. 5 and 6, the digital FM input signal on lead 58 is received at a first input of each of gates 101 and 102. Appropriate trigger pulses are received over leads 64 at a second input of each of gates 101 and 102. The appropriate trigger pulses first activate gate 101 for at least a portion of the weld period during which the solid-to-liquid phase transformation occurs in the weld area, and then activate gate 102 for at least a portion of the post-weld period during which the liquid-to-solid phase transformation occurs in the weld area. The activation of gate 101 permits the pulses on lead 58, representing the stress-wave energy detected during the solid-to-liquid phase transformation of the weld nugget, to be gated into counter 104. The activation of gate 102 permits the pulses on lead 58, representing the stress-wave energy detected during the liquid-to-solid phase transformation of the weld area, to be gated into counter 105. The combination of encoder 57 and counters 104 and 105 function in accordance with the equation:

$$E = \int_O^T v2(t)dt$$

within a scale factor. The multiplier 70 squares the instantaneous waveform on lead 54, voltage control oscillator 74 provides a digital representation of the continuous integration of the squared waveform, and counters 104 and 105 provide a sum of the integration over the time period of the solid-to-liquid and liquid-to-solid phase transformations.

In FIG. 5 the energy counts stored in counters 104 and 105 are transmitted to display means 106 and 107, respectively, where the results can be visually observed or mechanically recorded for possible research purposes, and to a common comparator circuit 108. Comparator circuit 108 is adapted to subtract the count in counter 105 from the count in counter 104, to compare the net resultant value with a preset threshold value, and to generate a go or no-go signal on lead 62 dependent upon the results of the comparison.

An alternative arrangement for count and comparator circuit 60 is shown in FIG. 6. There, an up-down counter 112 replaces both the counters 104 and 105 and display means 106 and 107 of FIG. 5. In operation, when gate 101 is enabled, counter 112 counts the number of pulses transmitted on lead 58 in an increasing fashion. When gate 102 is next enabled, counter 112 then subtracts each pulse on lead 58 from the total count obtained during the period when gate 101 was activated. Comparator 114 compares the net value stored in counter 112, after gate 102 has been deactivated, with a preset threshold value to generate a go or no-go signal on lead 62 dependent on the results of the comparison. The go or no-go signal on lead 62 from count and comparator circuit 60 can be used to energize a visual or audible means (not shown) for indicating a good or bad weld.

It must, of course, be understood that (a) the greater the higher count in counter 104 differs from the count in counter 105, the greater the strength of the weld; and that (b) the preset threshold value corresponds to a minimal acceptable weld strength value, which value can be easily determined by, for example, destructively testing a number of sample welds formed using the present system, and correlating the determined strength with the measurements obtained in counters 104 and 105, or counter 112, for each of the sample welds.

It has been found that a relatively linear relationship exists between the net resultant stress wave energy value, as determined in comparator 108 of FIG. 5 and up-down counter 112 of FIG. 6, and the pull strength of a weld, regardless of the composition of each of articles 12 and 14. The relatively linear relationship exists independent of the weld energy supplied by welder 20 or the condition, such as cleanliness, of articles 12 and 14 at the interfacing surfaces being welded. Therefore, variations in weld energy or the condition of articles 12 and 14 will merely be reflected in variations in stress-wave energy along the linear curve, and in turn, in the strength of the weld.

The properly timed trigger pulses transmitted on leads 64 to gates 101 and 102 are preferably provided by a detecting means 66 positioned in welder 20 and a shaping circuit 68 connected between detecting means 66 (FIG. 1) and gates 101 and 102. Detecting means 66 is positioned in welder 20 to both detect the presence of a weld pulse as capacitor 26 discharges, and generate a signal in response thereto on leads 67 to shaping and timing circuit 68. Detecting means 66 can comprise any known form, such as, for example, a toroidal coil detector mounted in the secondary circuit of welder 22. Shaping and timing circuit 68 can comprise any known circuit which receives the signal from detecting means 66 and generates a trigger pulse to (a) gate 101 during the weld period where at least the solid-to-liquid phase transformation interval occurs in the weld area, and (b) gate 102 during the post-weld period where at least the liquid-to-solid phase transformation interval occurs in the weld area.

Figure 2:
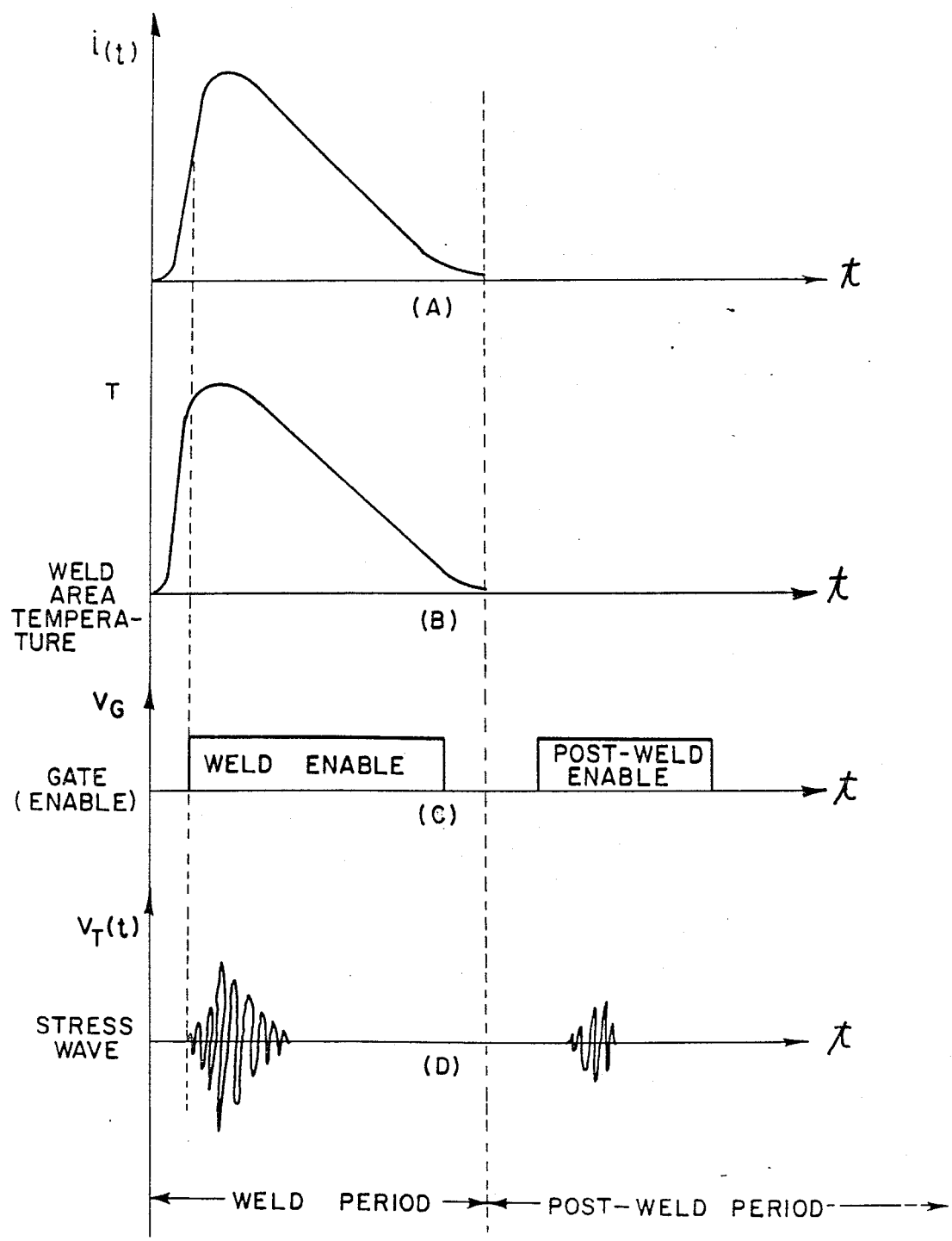
FIG. 2 illustrates various waveforms of the type which are displayed on an oscilloscope shown for purposes of explaining the present invention.

Referring particularly to FIG. 2, waveforms (A) to (D) typically illustrate various waveforms as they might normally appear on an oscilloscope connected to appropriate portions of the present weld evaluation system. Waveform (A) depicts the current pulse across the weld interface as delivered by secondary winding (S) of transformer 30 to electrodes 16 and 18 upon closure of switch 28 in welder 20. Waveform (B) depicts temperature variations occurring in the weld area in response to the current pulse of waveform (A) passing through the weld interface between articles 12 and 14. The temperature attains a peak during the period where melting or plastic deformation in the weld area occurs. Waveform (C) illustrates typical trigger pulses generated by shaping and timing circuit 68 which are transmitted to gating circuits 101 and 102 over leads 64. The weld enable pulse is used to enable gate 101 while the post-weld enable pulse is used to enable gate 102. Waveform (D) depicts stress waves detected by sensor 40 during the solid-to-liquid phase transformation interval (during weld period) and the liquid-to-solid phase transformation interval (during post-weld period). Typical waveforms found at various portions of the present system are also shown in FIGS. 1 and 3.

It is to be understood that the above-described embodiments are simply illustrative of the principles of the invention. Various other modifications and changes may be made by those skilled in the art which will embody the principles of the invention and fall within the spirit and scope thereof.

What is claimed is:

1. A method for the real-time, non-destructive evaluation of a weld comprising the steps of:
    a. measuring stress-wave energy emitted by the material deformation during the solid-to-liquid phase transformation of the weld area;
    b. measuring stress-wave energy emitted from cracks developing during the post-weld liquid-to-solid phase transformation of the weld area; and
    c. determining the strength of said weld by measuring the difference between the stress-wave energy measured during the solid-to-liquid phase transformation of the weld area and the stress-wave energy measured during the post-weld liquid-to-solid phase transformation.

2. A method according to claim 1 comprising the additional step of:
   d. generating an output signal indicative of a good weld when the magnitude of difference measurement exceeds a predetermined value.

3. A method for the real-time, non-destructive evaluation of a weld comprising the steps of:
   a. measuring stress-wave energy emitted by the material deformation during the solid-to-liquid phase transformation of the weld area;
   b. measuring stress-wave energy emitted from cracks developing during the post-weld liquid-to-solid phase transformation of the weld area;
   c. generating an electrical signal representative of the magnitude of the difference between the stress-wave energy measured during the solid-to-liquid phase transformation of the weld area and the stress-wave energy measured during the post-weld liquid-to-solid phase transformation of the weld area; and
   d. generating an output signal indicative of an acceptable weld when the magnitude of the difference determined in step (c) exceeds a predetermined value.

4. Apparatus for detecting and measuring stress waves propagating from a weld area between a first and a second workpiece being welded during a first solid-to-liquid phase transformation interval and a second liquid-to-solid phase transformation interval in the weld area for the real-time, non-destructive evaluation of said weld, the apparatus comprising:
   a. a sensor for detecting stress waves propagating in the material of said workpieces and generating an electrical output representative of the detected waves;
   b. a first signal processing means comprising:
      i. an amplifier for amplifying the electrical output from said sensor; and
      ii. a band-pass filter connected to the output of said amplifier for generating an analog output signal within a pass-band falling outside the range of frequencies normally generated by components in proximity to the apparatus; and
   c. second signal-processing means, connected to the output of said first-processing means, for measuring the stress-wave energy during said first solid-to-liquid phase transformation interval and said second liquid-to-solid phase transformation interval in said weld area, and thereafter determining the difference between the measurements of said first and second phase transformation intervals to provide a measurement of the strength of said weld.

5. Apparatus according to claim 4 wherein said apparatus further comprises:
   d. means for generating an output signal to indicate a good weld when the magnitude of the difference between the measurements of said first and second phase transformation intervals exceeds a predetermined value.

6. Apparatus according to claim 4 wherein said second signal-processing means comprises:
   i. encoding means, connected to the output of said first signal processing means, for generating a digital signal indicative of the energy of the output signal of said first signal-processing means; and
   ii. means for counting the digital pulses from said encoding means during said first solid-to-liquid phase transformation interval and said second liquid-to-solid phase transformation interval of said weld area, and thereafter determining the difference between said first and second transformation interval counts.

7. Apparatus according to claim 6 wherein said apparatus further comprises:
   d. means for generating an output signal to indicate a good weld when the magnitude of the difference between said first and second transformation interval counts exceeds a predetermined value.

8. Apparatus according to claim 4 wherein said second signal-processing means comprises:
   i. encoding means, connected to the output of said first signal processing means, comprising:
      a multiplier circuit for squaring the output signal from said first signal processing means, and
      voltage control oscillator circuitry connected to said multiplier circuit for generating a digital frequency-modulated signal indicative of the energy of said squared signal from said multiplier circuit; and
   ii. means for counting the digital pulses from said encoding means during said first solid-to-liquid phase transformation interval and said second liquid-to-solid phase transformation interval of said weld area, and thereafter determining the difference between said first and second transformation interval counts.

9. Apparatus according to claim 8 wherein said apparatus further comprises:
   d. means for generating an output signal to indicate a good weld when the magnitude of the difference between said first and second transformation interval counts exceeds a predetermined value.

10. Apparatus according to claim 8 wherein said voltage-control oscillator circuitry comprises:
   a plurality of window comparators, each window comparator being adapted to both compare the squared signal from said multiplier circuit with a predetermined amplitude range representing a different portion of the maximum possible amplitude range for said squared signal, and generate an enable signal in response to the amplitude of said squared signal being within said respective predetermined amplitude range; and
   a plurality of voltage-control oscillators, each oscillator being associated with a separate one of said plurality of window comparators and adapted to generate a digital frequency-modulated signal, within a different predetermined frequency range, indicating the energy in said squared signal in response to said enable signal from the associated window comparator.

* * * * *

UNITED STATES PATENT OFFICE
CERTIFICATE OF CORRECTION

Patent No. 3,965,726        Dated June 29, 1976

Inventor(s) Sotirios John Vahaviolos

It is certified that error appears in the above-identified patent and that said Letters Patent are hereby corrected as shown below:

In the specification, Column 1, line 31, "machine design" should read --Machine Design--; Column 5, line 10, the equation " $E = \int_0^T v2(t)dt$ " should read -- $E = \int_0^T v^2(t)dt$ --.

Signed and Sealed this

Fourteenth Day of September 1976

[SEAL]

*Attest:*

RUTH C. MASON        C. MARSHALL DANN
*Attesting Officer*        *Commissioner of Patents and Trademarks*